United States Patent
Risman et al.

(10) Patent No.: US 10,186,780 B2
(45) Date of Patent: Jan. 22, 2019

(54) MICROWAVE ANTENNA APPLICATOR

(71) Applicants: Per Olov Risman, Härryda (SE);
Magnus Otterskog, Arboga (SE);
Nikola Petrovic, Västerås (SE)

(72) Inventors: Per Olov Risman, Härryda (SE);
Magnus Otterskog, Arboga (SE);
Nikola Petrovic, Västerås (SE)

( * ) Notice: Subject to any disclaimer, the term of this patent is extended or adjusted under 35 U.S.C. 154(b) by 261 days.

(21) Appl. No.: 15/309,015

(22) PCT Filed: May 4, 2015

(86) PCT No.: PCT/SE2015/000022
§ 371 (c)(1),
(2) Date: Nov. 4, 2016

(87) PCT Pub. No.: WO2015/171033
PCT Pub. Date: Nov. 12, 2015

(65) Prior Publication Data
US 2017/0077609 A1    Mar. 16, 2017

(30) Foreign Application Priority Data

May 5, 2014 (SE) ...................... 1400222

(51) Int. Cl.
*H01Q 9/04* (2006.01)
*H01Q 13/24* (2006.01)
(Continued)

(52) U.S. Cl.
CPC ......... *H01Q 9/0485* (2013.01); *A61B 5/0507* (2013.01); *A61B 18/1815* (2013.01);
(Continued)

(58) Field of Classification Search
CPC . A61B 18/1804; A61B 18/1814; A61B 18/18; A61B 18/1815; H01Q 13/085;
(Continued)

(56) References Cited

U.S. PATENT DOCUMENTS 3,509,572 A * 4/1970 Barbano ............... H01Q 11/10
343/792.5
4,282,887 A    8/1981 Sterzer
(Continued)

FOREIGN PATENT DOCUMENTS

GB    2 403 148 A    12/2004

OTHER PUBLICATIONS

International Search Report (PCT/ISA/210) dated Jul. 31, 2015, by the Swedish Patent Office as the International Searching Authority for International Application No. PCT/SE2015/000022.
(Continued)

*Primary Examiner* — Tho G Phan
(74) *Attorney, Agent, or Firm* — Buchanan Ingersoll & Rooney P.C.

(57) ABSTRACT

A new and comparatively small type of open-ended microwave applicators has been disclosed. They are for example suitable for transmission into and reception from contacting objects such as protruding human bodyparts for inhomogeneity detection by tomographic methods. The applicators according to the invention are of the dielectric-filled open-ended ridged rectangular $TE_{10}$ type, with an insert filling the ridge and having a higher permittivity than the surrounding space. The shape of the insert can be as a frustrum pyramid towards the opening. The overall design promotes narrow beamwidths and minimizes nearfields and surface wave excitation.

7 Claims, 2 Drawing Sheets

(51) Int. Cl.
*A61B 18/04* (2006.01)
*A61B 18/18* (2006.01)
*H01Q 13/08* (2006.01)
*A61B 5/05* (2006.01)
*H01P 3/12* (2006.01)
*H01P 3/123* (2006.01)
*A61N 5/04* (2006.01)
*A61B 18/00* (2006.01)

(52) U.S. Cl.
CPC .............. *H01P 3/122* (2013.01); *H01P 3/123* (2013.01); *H01Q 13/085* (2013.01); *H01Q 13/24* (2013.01); *A61B 2018/00607* (2013.01); *A61B 2018/183* (2013.01); *A61N 5/04* (2013.01)

(58) Field of Classification Search
CPC ........ H01Q 9/04; H01Q 9/0485; H01Q 13/24; H01P 3/122; H01P 3/123
See application file for complete search history.

(56) References Cited

U.S. PATENT DOCUMENTS

| | | | |
|---|---|---|---|
| 4,353,074 A * | 10/1982 | Monser | H01Q 21/08 343/776 |
| 4,392,039 A | 7/1983 | Risman | |
| 6,287,302 B1 | 9/2001 | Berube | |
| 6,471,696 B1 * | 10/2002 | Berube | A61B 18/1492 606/33 |
| 7,052,491 B2 * | 5/2006 | Erb | A61B 18/14 606/14 |
| 8,059,059 B2 * | 11/2011 | Bonn | A61B 18/18 343/793 |
| 8,262,703 B2 * | 9/2012 | Prakash | A61B 18/18 606/261 |
| 8,870,860 B2 * | 10/2014 | Lee | A61B 18/1815 606/33 |
| 9,161,811 B2 * | 10/2015 | Cronin | A61B 18/18 |
| 2007/0043346 A1 | 2/2007 | Cronin | |
| 2011/0077633 A1 | 3/2011 | Bonn et al. | |
| 2011/0213352 A1 | 9/2011 | Lee et al. | |

OTHER PUBLICATIONS

Written Opinion (PCT/ISA/237) dated Jul. 31, 2015, by the Swedish Patent Office as the International Searching Authority for International Application No. PCT/SE2015/000022.

Gibbon, D. et al., "A Comparison of a Wide-Slot and a Stacked Patch Antenna for the Purpose of Breast Cancer Detection", IEEE, Transactions on Antennas and Propagation, vol. 58, No, 3, pp. 665-674, Mar. 2010.

Bourqui, J, et al., "Balanced Antipodal Vivaldi Antenna with Dielectric Director for Near-Field Microwave Imaging", vol. 58, No. 7, pp. 2318-2326, Jul. 2010.

\* cited by examiner

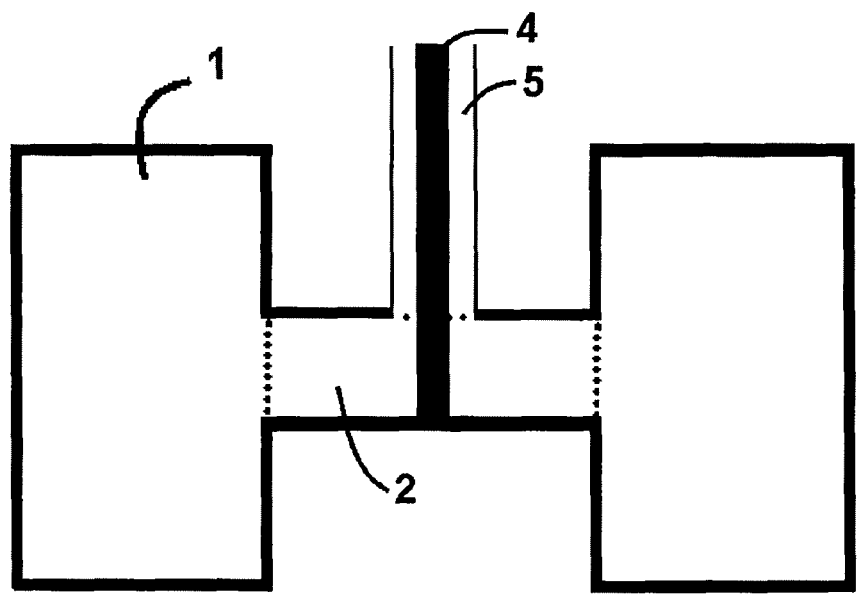
Figure 1
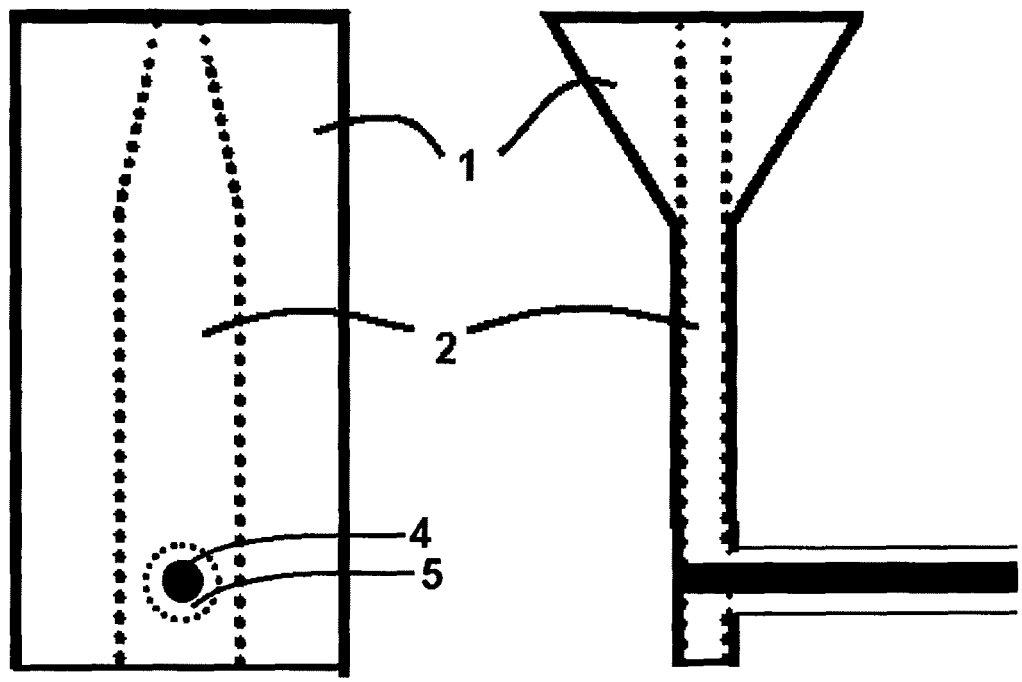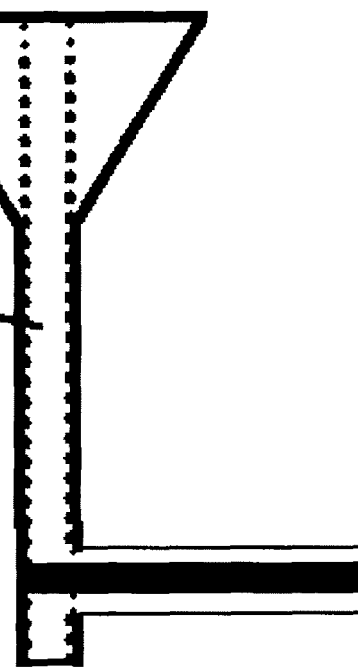
Figure 2     Figure 3

MICROWAVE ANTENNA APPLICATOR

FIELD OF THE INVENTION

The present invention is related to the field of open-ended frequency broadband microwave applicators. In particular, the applicators are intended for acting as transmitting and receiving antenna structures in close proximity to or contacting protruding human tissue such as female breasts, for tomographic investigations of irregularities caused by diseases such as cancer.

However, there are also a number of other applications both in industry and for medical so-called hyperthermia treatments with the aim to partially and geometrically selectively destroy tissue or coagulate bloodflow during surgery.

BACKGROUND OF THE INVENTION

There are several kinds of prior art antennas described in the literature for the general purposes above. Examples are:
1. Coaxial endfire applicator.—A typical example is described in U.S. Pat. No. 6,287,302. These have the advantage over more complicated systems by coaxial transmission lines being inherently frequency broadband. However, the TEM mode in the applicator is of the nearfield type, meaning that wave propagation as the plane-wave TEM type necessary in free space or a non-enclosed medium does not take place. The field matching is therefore poor and only a thin zone nearby of the absorbing object under study (OUS) will be significantly treated. As a consequence, using such systems with multiple antennas for signal detection across an OUS consisting of e.g. a female breast is therefore not possible. Furthermore and due to the nearfield absorption, the system must either be resonant (i.e. single frequency) or have a very low coupling factor (i.e. a low power efficiency). The former is indicated in the referred patent. Additionally, the heating pattern in the OUS will be mainly peripherally ring-shaped (as indicated in the referred patent), but this is not due to any ray-like propagation as indicated in FIG. 3 of the referred patent, but instead simply due to the primary circular magnetic field creating an electric field by Faraday's law.—However, it is of course possible to create a distinguishable microwave mode pattern in a coaxially fed high permittivity body. This is the next example 2.
2. Circular $TM_{01}$ mode endfire applicator.—This is described in U.S. Pat. No. 4,392,039. A high permittivity dielectric filling is necessary for both achieving a suitably small applicator diameter when fed by an inexpensive ISM 2450 MHz band microwave generator, and for achieving a desirable so-called magnetic wall effect at resonance resulting in the resonant standing wave in the applicator having a dominant electric field parallel to the OUS interface; see FIG. 2 in the example patent. The permittivity of the low loss dielectric filling is thus significantly higher than that of the OUS, so titanium dioxide ($\varepsilon'=90$) is preferred. The heating pattern in the OUS then typically becomes flat ellipsoidal, with a depth away from the blunt end of the applicator of up to about five millimeters. Again, this field cannot radiate further due to field mismatching to a TEM wave in a free medium.
3. Other circular endfire applicators using a rotationally symmetric microwave mode of the kinds in the first and second example.—Two examples are US 2011/0077633 A1 and GB 2 403 148 A. Elaborations are made to provide a better coupling factor to the OUS, for an acceptably wide range of OUS permittivities. However, a field pattern of the coaxial TEM type or the related circular $TM_{01}$ type at the OUS remains.

All antenna systems referred to so far are nearfield and suitable for ablation and other spotheating purposes, but not at all for multiple antenna signal transmission and measurements through an OUS for microwave tomographic purposes. An advantage is, however, that there is no peripheral electric field perpendicularly to the OUS surface outside the applicator, which would cause microwave surface waves which in turn would cause unwanted possible microwave exposure to the operator.

4. Helix antennas.—These have the property of the circular polarisation reversing upon signal reflection, which is advantageous for detection of microwave diffraction of internal inhomogeneities in OUTs. They are, however, rather narrowband in the frequency domain. Since the contacting tissue has a much higher permittivity than air, the antennas must be miniaturised and impedance matched by casting into a high permittivity microwave transparent material. This considerably complicates the practical design.
5. Patch antennas.—A typical example is described in the paper *A Comparison of a Wide-Slot and a Stacked Patch Antenna for the Purpose of Breast Cancer Detection* in IEEE TRANSACTIONS ON ANTENNAS AND PROPAGATION, VOL. 58, NO. 3, MARCH 2010. These are better in frequency broadband but suffer from impedance matching problems necessitating their immersion in an external liquid with comparable permittivity to that of the tissue. In practise such liquid layer constitutes a bolus, i.e. is intended for providing impedance matching improvement and "geometric control" of the overall OUS, as well as—by its dielectric losses—a reduction of disturbing stray propagation of the microwaves. However, the bolus must then be in very close contact with the OUS, which may cause patient discomfort.
6. Vivaldi antennas.—A typical state-of-the-art example is described in the paper *Balanced Antipodal Vivaldi Antenna With Dielectric Director for Near-Field Microwave Imaging* in IEEE TRANSACTIONS ON ANTENNAS AND PROPAGATION, VOL. 58, NO. 7, JULY 2010.—One can say that vivaldi antennas are developments based on so-called E-plane ridged flared horn antennas for microwave communication An E-plane horn extends (flares) in only the direction of the narrow walls in a rectangular $TE_{10}$ waveguide. Vivaldi antennas are inherently frequency broadband (e.g. in the literature example from about 1 to 12 GHz) which makes them suitable for use with pulsing techniques, as in common radar systems. They may also be designed to have a favourable beamwith, which is a very important performance factor. However, the electromechanical design is complicated and requires very tight tolerances, resulting in quite expensive antennas. Also their physical size is quite large; about 40 mm in width for 1 to 3 GHz operation in the literature example.
7. Endfired ridged $TE_{10}$ waveguides as applicators for hyperthermia treatment.—An example is in U.S. Pat. No. 4,282,887. The whole waveguide cross section is filled with a homogeneous high permittivity dielectric (water in this case). A combination of this and the ridged design results in a much reduced critical frequency than with no ridges and no filling. This makes it possible to employ a frequency lower than microwaves with an applicator of suitable end opening dimensions for treatment of quite large bodyparts such as thighs. The use of water having a permittivity higher than that of the human tissue can be employed to create a resonant system which increases the energy efficiency. The low frequency has the advantage of a deeper penetration depth of the propagation into the OUS having a permittivity comparable to that of the waveguide filling.

There is thus a need for contacting antenna applicators which:
- are physically small while maintaining a desirable lowest frequency of operation of about 1 GHz;
- have a frequency bandwidth up to 3 to 4 GHz, i.e. intended for frequency hopping continuous wave operation. Higher frequencies are normally deprecated due to the strong attenuation across large OUSs such as female breasts;
- allow (and are thus designed for) direct contact to the surface (i.e. skin) of the OUS;
- have small contact area dimensions for providing very small airgaps to or distortion of the OUS;
- provide minimal nearfields, which are non-radiating fields typically having a strong and negative influence on the quality of the microwave transmission between antennas. This is since very small OUS irregularities at the contacting area have a large influence;
- cause minimal excitation of unwanted surface waves along the OUS periphery, such waves are characterised by an electric field component essentially perpendicular to the OUS surface;
- provide a narrow radiation lobe, also resulting in minimal excitation of unwanted surface waves along the OUS periphery;
- are uncomplicated and inexpensive to manufacture.

SUMMARY OF THE INVENTION

The object of the present invention is to address the problems described above.

With given dimensions, rectangular $TE_{10}$ type waveguides allow propagation of the lowest frequency which is the so-called normal mode. Their field pattern at a blunt opening is also quite well-matched to free space propagating TEM waves. It is 2 for the standard waveguides used for transmission. Their frequency bandwidth (i.e. that over which only the $TE_{10}$ mode can exist) is then also a factor 2.

A ridged $TE_{10}$ type waveguide has the further advantage of increased mode stability (i.e. other modes not being possible) over a wider frequency range. Furthermore, its lowest transmission operating frequency is also lower with given a dimension.

The factors above are known, as is the possibility of filling the ridged waveguide with a dielectric to further reduce its size as well as its impedance matching to a human OUS. The linear size reduction factor then becomes $\sqrt{\varepsilon'}$, where $\varepsilon'$ is the real permittivity ("dielectric constant") of the filling dielectric.

Such antenna applicators do, however neither provide a very narrow beamwidth of the propagation away from the applicator antenna nor minimised sideways excitation of surface waves along the OUS.

According to the invention, a dielectric filling is employed in a symmetrically ridged $TE_{10}$ type waveguide, and a second partially and symmetrically filling object— insert—with a higher permittivity than that of the first filling. The first dielectric filling has a lower $\varepsilon'$ than that of the OUS average. The insert has an $\varepsilon'$ comparable to that of the OUS average and has a frustrum foursided pyramidal shape with its endfire end being smaller than the ends towards the waveguide excitation. This changes the field pattern internally and in particular at the waveguide opening in such a way as to provide both a more narrow beamwidth and reduced sidelobe and surface wave excitation along the OUS.

BRIEF DESCRIPTION OF THE DRAWINGS

The geometrical definitions and the features of the present invention are illustrated on the following appended drawings, on which FIG. 1 shows a view across the propagation direction in the ridged waveguide.

FIGS. 2 and 3 show the views in the two other co-ordinate directions.

DETAILED DESCRIPTION

Figure 4:
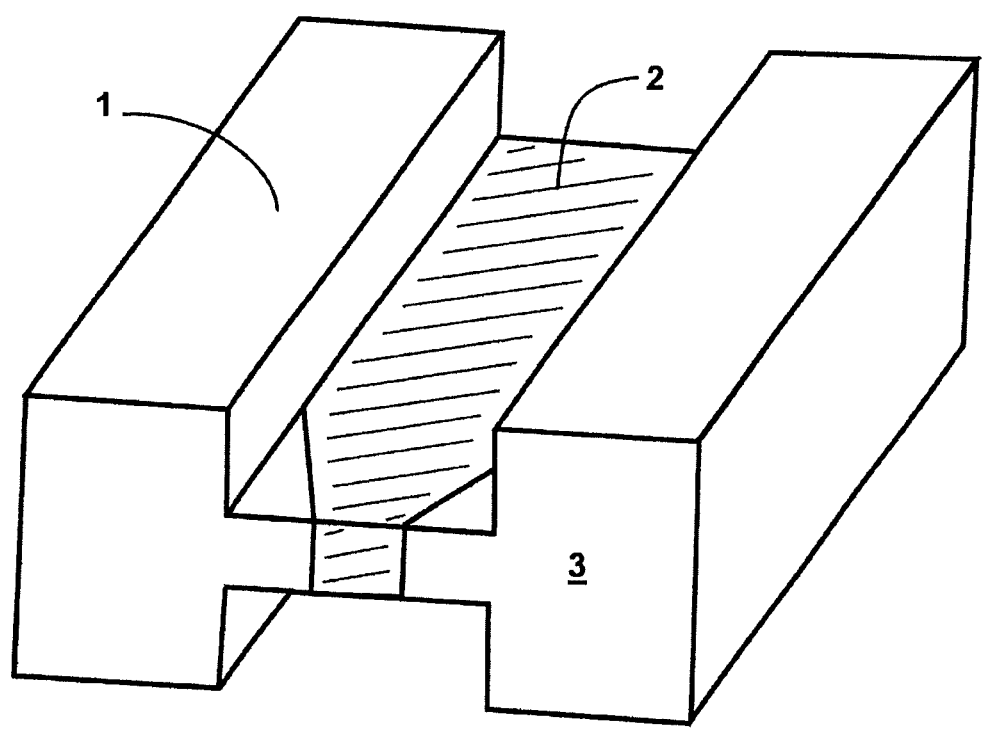
FIG. 4 shows a perspective view of the front portion of the ridged waveguide. A possible thin protective microwave transparent cover at the front end is not shown The continuous lines in FIGS. 1, 2 and 3 indicate the exterior of the antenna and its feed. This is metallic except at the (upper) opening which is intended to contact the OUS. The dotted lines in the same figures indicate the shape of the insert 2 with a higher permittivity than the filling 1; the dotted circle in FIG. 2 indicates the outer diameter of the coaxial feed, and the thinner dotted line in FIG. 3 indicates the boundary between the insert 2 and the (typically PTFE) filling in the standard-type coaxial feedline. The parallel thin lines in FIG. 4 indicate the surfaces of the insert 2.

One embodiment of an applicator according to the present invention is now described, with reference to the Figures.

Typical overall inner cross section dimensions of the transmission part of the waveguide (FIG. 1) are about 9 mm×15 mm with ridge width 8 mm and inter-ridge distance 2 mm, for a cutoff frequency about 1 GHz with a filling 1 with $\varepsilon'$ about 17 and insert 2 with $\varepsilon'$ about 35. The reasons for these choices of permittivities are:

1) Both have to be quite high, for obtaining miniaturisation of the waveguide by the linear factor $\sqrt{\varepsilon'}$; the waveguide is also ridged for the same reason.
2) The permittivity e of the insert 2 is to be rather close to the permittivity of the OUS, since this will minimise wave reflections at the interface between the antenna end and the OUS. Since typical OUS tissues have $\varepsilon'$ between 25 and 50 in the frequency range 1 to 3 GHz of operation, a suitable dielectric 2 is compact sintered zirconium dioxide having $\varepsilon'$ about 35.
3) For fulfilling two important embodiments of the invention described later, the dielectric 1 surrounding the insert 2 should have a permittivity $\varepsilon'$ about half that of the insert 2.

The insert 2 fills the ridge and thus has cross section dimensions of about 2 mm×8 mm in its transmission part. The relatively quite narrow gap between the two ridge surfaces provides a very significant reduction of the critical $TE_{10}$ normal mode frequency. For example the cutoff frequency of a ridged waveguide as described and with a complete filling with $\varepsilon'=17$ has a cutoff frequency of 1.31 GHz; without the ridge it becomes 2.41 GHz. The ridge filling by the ceramic insert 2 is also of practical importance since its two opposing wide sides can be metalised for reliable function and the coaxial feed of the antenna is then by a reliable configuration consisting of a metal pin (probe) 4 from a coaxial line 5 going all the way through a hole in the ceramic insert 2, with its far end welded or soldered to the waveguide wall. A suitable pin diameter is about 1 mm and it must of course be filling the hole in the ceramic.

The function of the permittivity quotient of about ½ between the surrounding dielectric 1 and the higher-$\varepsilon'$ insert 2 and its shape is now described, in terms of electric field (E) geometry. At the opening of a constant cross section ridged waveguide with homogeneous filling, the E field wavefront will no longer be plane but be bulging outwards. This will strongly contribute to nearfield creation, i.e. fields no longer being parallel to the OUS surface. If, however, there is a filling in the ridge with higher $\varepsilon'$ than its surrounding, the central part of the wavefront will become somewhat retarded due to the general phenomenon of slower speed of propagation in higher-$\varepsilon'$ substances. This will result in a more plane-like wavefront being created and thus in turn less nearfied excitation; this constitutes a first embodiment of the invention.

A further and second embodiment of the invention is that the front end part of the insert 2 is foursided frustrum pyramidal in only the wide (TE$_{10}$ waveguide a) direction. The end tip width can be as shown in FIGS. 2 and 4. The length of this frustrum pyramid in the direction of wave propagation is typically in the order shown on FIGS. 2 and 3, i.e. in the order of the overall waveguide a dimension, and is for providing better impedance relationships in the varying cross section part, and for avoiding a too strong concentration of field energy to the ridge end facing the OUS.

As not shown in FIGS. 2, 3 and 4 a further embodiment is not to let the ceramic insert go all the way to the antenna opening. Positive reasons for this are that the field pattern will be smoother at the opening and thus reduce very local nearfield effects, and that a continuous material at the opening will provide better mechanical sealing. However, this distance should be small—in the order of 1 mm or slightly less in the example of overall waveguide cross section about 9 mm×15 mm with ridge width 8 mm and inter-ridge distance 2 mm, for a cutoff frequency about 1 GHz with a filling 1 with $\varepsilon'$ about 16 and insert 2 with $\varepsilon'$ about 35.

It is also shown in FIG. 3 that it may be advantageous to let the waveguide opening region be horn-like in the narrow (TE$_{10}$ waveguide b) direction, i.e a so-called E-plane horn. The function of this additional embodiment is to reduce the beamwidth in that plane, while not exceeding the overall antenna opening maximum dimension of about 15 mm. The function of this embodiment is related to that of flared horn antennas with a central higher-$\varepsilon'$ central protrusion rather than metallic ridge-like elements centrally in the wide (TE$_{10}$ waveguide a) sides.

It is in this context important to note that the primary goal with tomographic set-ups with transmitting and receiving antennas located around the OUS is to receive signals which have been reflected and diffracted by internal dielectric inhomogeneities and are received by another antenna. Therefore, "false direct" signals propagated as surface wave along the OUS surface are detrimental and will reduce the dynamic range of the system. Furthermore, the intensity of the transmitter signal can almost always be increased without any health or local OUS tissue heating effects. This results in reducing "false direct" and other disturbing signal parts, which is imperative for the system function. Geometrically small antennas with minimised beamwidths are therefore more important than some decibels of impedance mismatching.

This summary has presented a number of embodiments of the present invention, which are summarised in the appended claims.

The invention claimed is:

1. An endfire antenna applicator consisting of an open-ended ridged rectangular TE$_{10}$ waveguide operating within a predetermined microwave frequency interval, intended for transmitting or receiving signals through an object under study (OUS) characterising its dielectric inhomogeneities, characterised in having a solid, rectangular cross section dielectric insert in the transmission part of the ridge, with a higher permittivity than in the remaining space of the waveguide.

2. An antenna applicator as in claim 1, where the cross section of the insert is successively and symmetrically reduced in the waveguide a (wide)dimension towards the open end in the direction of propagation, over a distance corresponding to approximately the overall waveguide a dimension.

3. An antenna applicator as in claim 1, where the dielectric insert ends at the opening plane.

4. An antenna applicator as in claim 1, where the dielectric insert ends a distance of 1 mm or less away from the opening plane for systems with about 1 to 3 GHz operating frequency range.

5. An antenna applicator as in claim 1, characterised in the dielectric insert having a permittivity within ±30% of that of the OUS, and the surrounding dielectric in the waveguide having a permittivity about half of that of the insert.

6. An antenna applicator as in claim 1, characterised in the waveguide end region being flared in its narrow (±b) directions and there filled with the same material as the waveguide filling.

7. An antenna applicator as in claim 1, characterised in the feed being from a TEM coaxial line near its closed end, by a metal probe going all the way through the ridge.

* * * * *